US009254437B2

(12) United States Patent
Short et al.

(10) Patent No.: US 9,254,437 B2
(45) Date of Patent: Feb. 9, 2016

(54) INTERACTIVE GAMING ANALYSIS SYSTEMS AND METHODS

(71) Applicant: Electronic Entertainment Design and Research, Carlsbad, CA (US)

(72) Inventors: Gregory T. Short, Carlsbad, CA (US); Geoffrey C. Zatkin, Encinitas, CA (US); Christopher R. Taylor, Escondido, CA (US)

(73) Assignee: Electronic Entertainment Design and Research, Carlsbad, CA (US)

( * ) Notice: Subject to any disclaimer, the term of this patent is extended or adjusted under 35 U.S.C. 154(b) by 0 days.

(21) Appl. No.: 13/870,794

(22) Filed: Apr. 25, 2013

(65) Prior Publication Data

US 2013/0288777 A1   Oct. 31, 2013

Related U.S. Application Data

(60) Provisional application No. 61/638,343, filed on Apr. 25, 2012.

(51) Int. Cl.
| | |
|---|---|
| *A63F 13/00* | (2014.01) |
| *A63F 13/98* | (2014.01) |
| *A61B 5/16* | (2006.01) |
| *A63F 13/45* | (2014.01) |
| *A63F 13/212* | (2014.01) |
| *A61B 5/00* | (2006.01) |

(52) U.S. Cl.
CPC . *A63F 13/02* (2013.01); *A61B 5/16* (2013.01); *A63F 13/00* (2013.01); *A63F 13/212* (2014.09); *A63F 13/45* (2014.09); *A61B 5/165* (2013.01); *A61B 5/4842* (2013.01); *A61B 5/4848* (2013.01); *A61B 5/6803* (2013.01); *A61B 5/6804* (2013.01); *A61B 5/6896* (2013.01); *A61B 5/7264* (2013.01)

(58) Field of Classification Search
CPC .............. A63F 13/10; A63F 2300/10; A63F 2300/1012; A63F 2300/1056; A63F 2300/5546; A63F 2300/558
USPC ........................................ 463/7, 9, 16, 23, 29
See application file for complete search history.

(56) References Cited

U.S. PATENT DOCUMENTS

| | | | |
|---|---|---|---|
| 5,474,295 A | 12/1995 | Demshuk | |
| 6,299,452 B1 | 10/2001 | Wasowicz et al. | |
| 6,648,760 B1* | 11/2003 | Nicastro | 463/23 |
| 2002/0076677 A1* | 6/2002 | Wasowicz et al. | 434/178 |
| 2003/0027639 A1* | 2/2003 | Peterson et al. | 463/42 |
| 2004/0014021 A1 | 1/2004 | Suleiman | |
| 2004/0212149 A1 | 10/2004 | Farmer | |
| 2006/0127871 A1 | 6/2006 | Grayson | |
| 2008/0070682 A1 | 3/2008 | Woody | |
| 2012/0017232 A1 | 1/2012 | Hoffberg et al. | |
| 2012/0197874 A1* | 8/2012 | Zatkin et al. | 707/722 |

OTHER PUBLICATIONS

Grammenos, D., "The Theory of Parallel Game Universes: A Paradigm Shift in Multiplayer Gaming and Game Accessibility", Gamasutra, Aug. 17, 2006, http://web.archive.org/web/20060821231407/http://www.gamasutra.com/features/20060817/grammenos_01.shtml.

* cited by examiner

*Primary Examiner* — James S McClellan
(74) *Attorney, Agent, or Firm* — Fish & Tsang, LLP

(57) ABSTRACT

An interactive gaming system is disclosed. The system comprises at least one sensor that conveys information to the system about the physical, intellectual, mental, emotional, psychological or other type of ability of a user. The system uses the information to assess the existence and extent of a disability, and then implements a change to an aspect of the gaming environment, thus optimizing the gaming experience for the game player by accounting for the game player's disabilities.

19 Claims, 7 Drawing Sheets

| Deviation Range | | | |
|---|---|---|---|
| 0%-10% | Disability Indicator 401a | Null | Disability Indicator 403a |
| 11%-20% | Disability Indicator 401b | Disability Indicator 402a | Disability Indicator 403b |
| 21%-30% | Disability Indicator 401c | Disability Indicator 402b | Disability Indicator 403c |
| ○○○ | | | |
| Over 100% | Disability Indicator 401d | Disability Indicator 402c | Disability Indicator 403c |

Figure 4

| Disability 501 | Sensor Data 502 | Sensor Data 503 | Sensor Data 504 |
|---|---|---|---|
| Disability Indicator 501a | Deviation Range 502a | Deviation Range 503a | Deviation Range 504a |
| Disability Indicator 501b | Deviation Range 502b | Deviation Range 503b | Deviation Range 504b |
| Disability Indicator 501c | Deviation Range 502c | Deviation Range 503c | Deviation Range 504c |
| Disability Indicator 501n | Deviation Range 502n | Deviation Range 503n | Deviation Range 504n |

Figure 5

INTERACTIVE GAMING ANALYSIS SYSTEMS AND METHODS

This application claims the benefit of U.S. Provisional Application No. 61/638,343, filed on Apr. 25, 2012. U.S. Provisional Application No. 61/638,343, and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is in the area of gaming technologies, in particular game aware accessories that improve a gaming experience for a user having one or more disabilities.

BACKGROUND

Computing devices have a number of uses, among the most popular being use in various games. The continued evolution of computing technology, including increased storage, faster processing times, and highly realistic displays, combined with high bandwidth networks have resulted in computers being able to provide highly realistic gaming experiences for users.

While game developers will often target products towards specific demographic audiences, there are limitations to this approach. For example, games are typically tailored to appeal to a specific age, demographic, or gender. This approach requires the assumption that in general, all users within the target demographic are of similar physical and intellectual ability, in order for the game experience to be relatively consistent from one user to the next.

Not all users are created equal, and there will be physical, intellectual, and even psychological differences among specific users that will result in a different game experience for each user. Where the game player or user is disabled, the gaming experience can be significantly less enjoyable depending on the nature and extent of the disability. With some disabilities, access to or perception of certain game content may be impossible.

There have been some previous attempts by others to assess or diagnose different types of disabilities. For example, U.S. Pat. No. 6,299,452 to Wasowicz et al., titled "Diagnostic System and Method for Phonological Awareness, Phonological Processing, and Reading Skill Test, filed Jul. 9, 1999, discusses the use of graphics based games to test a person's phonological abilities. Similarly, U.S. Patent Application publication 2004/0014021 to Suleiman title, "Apparatus and Method for Evaluating School Readiness", filed Jul. 17, 2002, discusses using computer-based games to evaluate whether a child is ready to begin school. Still, further, U.S. Patent Application publication 2006/0127871 to Grayson titled "Method and Apparatus for Teaching", filed Feb. 10, 2006, discusses tracking a student's progress through interactive computer lessons that allow the student to be assessed for learning disabilities based on those interactions.

Others have directed their efforts towards the development of games specifically tailored for disabled persons. For example, U.S. Pat. No. 5,474,295 to Demshuk titled "Game Apparatus for the Handicapped", filed Aug. 24, 1994, discusses a table game apparatus adapted for use by a person having a physical or mental handicap. U.S. Patent Application publication 2004/0212149 to Farmer titled "Social Skill Builder Game", filed Apr. 24, 2004, discusses a board game adapted to develop and improve behavior skills for children and adults with developmental disabilities. Similarly, U.S. Patent Application publication 2008/0070682 to Woody titled "Systems and Methods for Providing Education Games for Use by Young Children, and Digital Storage Medium for Storing the Educational Games Thereon", filed Aug. 15, 2007, discusses providing a controller that can be grasped by a young child or a person with a disability. These references also contemplate a priori constructed games or game elements to make a game accessible to a disabled person.

Despite these efforts, even games designed for disabled persons as a demographic group suffer from the same limitations as games designed for non-disabled players. Specifically, known games and gaming systems do not provide a way for the gaming system to interactively assess physical, intellectual or psychological limitations of an individual user, and then use that information to either tailor the gaming experience for the user, or as a means of developing a suggested "playlist" of games that are suitable given that user's specific characteristics and/or limitations.

Thus, the above references fail to appreciate that a game designer, specifically a computer game designer, requires insight into the characteristics and limitations of individual users in order to design a game with the broadest appeal and utility to a group of users who may have widely varying abilities and disabilities. Similarly, there is currently no known system that permits a user to be able to provide information about their particular abilities or disabilities in real-time in order to query a gaming system about which particular games might be most appropriate or most enjoyable based on their personal characteristics.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

SUMMARY OF THE INVENTION

The inventive subject matter provides apparatus, systems and methods in which one can tailor a gaming system for use by a handicapped user in order to optimize a gaming experience. In some embodiments the gaming system comprises one or more sensors that provide information about a user to the gaming system. These sensors may provide information about sensed conditions such as position in 3-D space, movement, acceleration and similar information about time and space. Sensors may be adapted to provide means through which to analyze physical, sensory, intellectual and/or psychological abilities of a user as they play a computer game.

Sensors may be self-reporting with respect to sensed conditions, or may interact with accessory systems such as video detection systems that are configured to locate the position of a sensor in 3-D space and then report data corresponding to the sensed conditions to a suitable receiver system such as a gaming analysis engine.

In some cases sensors may be temporarily affixed either to parts of the user's body, or to clothing, headgear, footwear or other such wearable apparel. In some cases, the sensors may be integrated into items of apparel worn by the user. For example, sensors can be located in shoes, gloves, hats, shirts, pants, headphones and the like in order to provide time and space information about virtually any point on the user's body. In another example, chemical sensors attached to a user's body can provide information about a person's blood sugar, blood alcohol level and other information that can be derived from measuring blood or sweat.

Data from the sensors can be transmitted to a gaming analysis engine adapted to receive and analyze the sensor data. The gaming analysis engine can receive the data from the sensors directly, or via the user interface or the game system, and evaluate sensor data collected as the user interacts with game or activity parameters. The gaming analysis engine can be configured to measure the ability of a user to respond to the game or activity in a variety of ways, such as physically, mentally, emotionally, intellectually, physiologically, etc.

Using data received from the sensors, the physical, sensory, intellectual, emotional, psychological, and other abilities of the user can be evaluated to indicate the existence and extent of one or more disabilities. The results of such evaluation can then be used to tailor the gaming experience through a game modification based on the existence and extent of a user's disability, such that the user gains optimal enjoyment or benefit from the game or activity. The information may also be used to query a gaming system and access a recommendation engine that is programmed to make suggestions to the user as to games or activities that might be most enjoyable or beneficial based on the existence or extent of a user's current disability by querying a game database.

The system can also be configured to maintain a log of inputs from users over times, such as from different times playing a game or engaging in an activity. Data can be maintained in a player database that can be accessed by the gaming analysis engine. The data received over time can be used to evaluate changes in user performance (improvement or degradation). These changes in performance can be used to continually update an individualized player database that is designed to refine suggestions of games or activities, or potentially to alert the user or health care professionals that performance is improving or declining, which in turn can be used in conjunction with traditional methods of recovery, therapy, rehabilitation and other treatments related to the determined disabilities.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 4 is an example of deviation data set in the form of a sensor deviation data set.

FIG. 5 is an example of a reference data set representing a disability.

DETAILED DESCRIPTION

It should be noted that while the following description is drawn to a computer/server based gaming analysis engines, various alternative configurations are also deemed suitable and may employ various computing devices including servers, interfaces, systems, databases, agents, peers, engines, controllers, or other types of computing devices operating individually or collectively. One should appreciate the such computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including the ability of a gaming system to monitor and adapt to a user in real time, based on sensor-based measurement of that user's various physical, intellectual and psychological abilities. The system further provides the technical effect of tailoring the user's gaming experience based on the system's evaluation of that user's relative abilities.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventive subject matter comprises an interactive system to enable a user or game player, and in particular a handicapped or disabled user or game player, to interact with a computer-based gaming system, and thereby to optimize an individual's experience with a game or activity.

Figure 1:
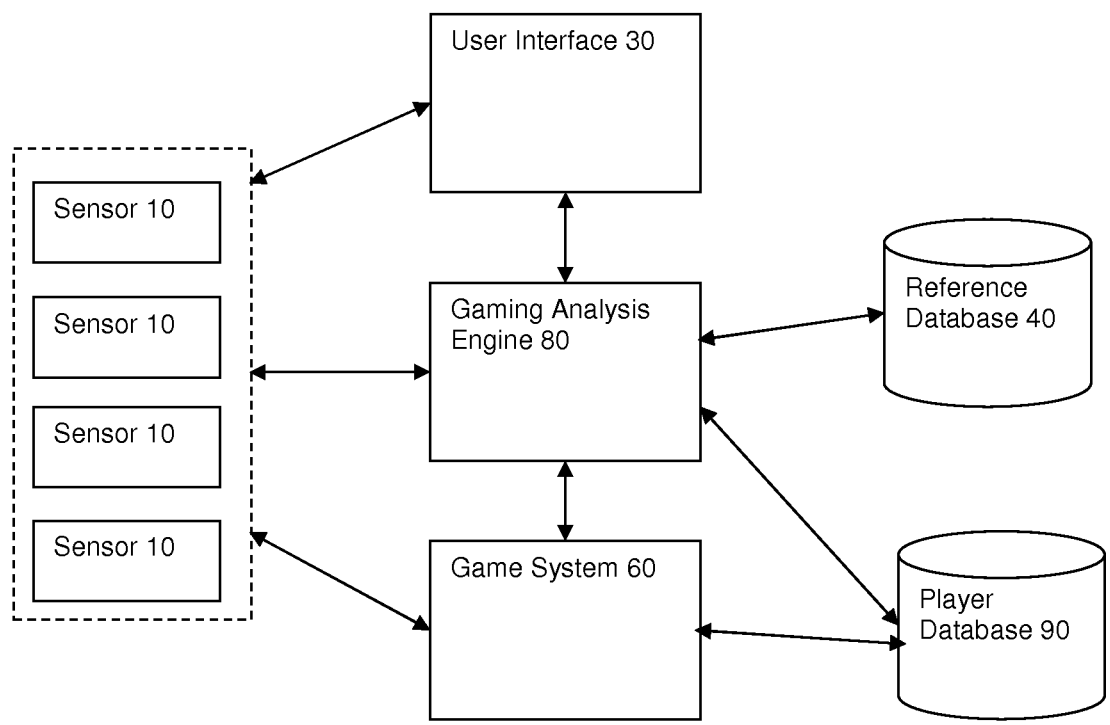
FIG. 1 is a schematic of an interactive system for optimizing a gaming experience.

FIG. 1 provides an overview of the system of the present inventive subject matter.

As shown in FIG. 1, an interactive sensor-based system can comprise one or more sensors 10 communicatively coupled to a gaming analysis engine 80. The system can include a game system 60 and can further include a user interface 30. Each of the game system 60 and the user interface 30 can be communicatively coupled with the other components of the system. The connections between the components of the system can comprise local or long-range communication interfaces, and can comprise wireless or wired communication interfaces.

FIG. 1 provides examples of how sensors 10 can be communicatively coupled with the gaming analysis engine 80. A system may have, at any particular time, sensors connected via one or more of these alternatives. Sensors 10 can be connected directly to the gaming analysis engine 80 or via one or more of the game system 60 and the user interface 30.

Optionally, one or more of sensors 10 can be integral to the game system 60 or user interface 30. Each individual sensor 10 can use one or more of these connection alternatives to connect to the gaming analysis 80.

Figure 2:
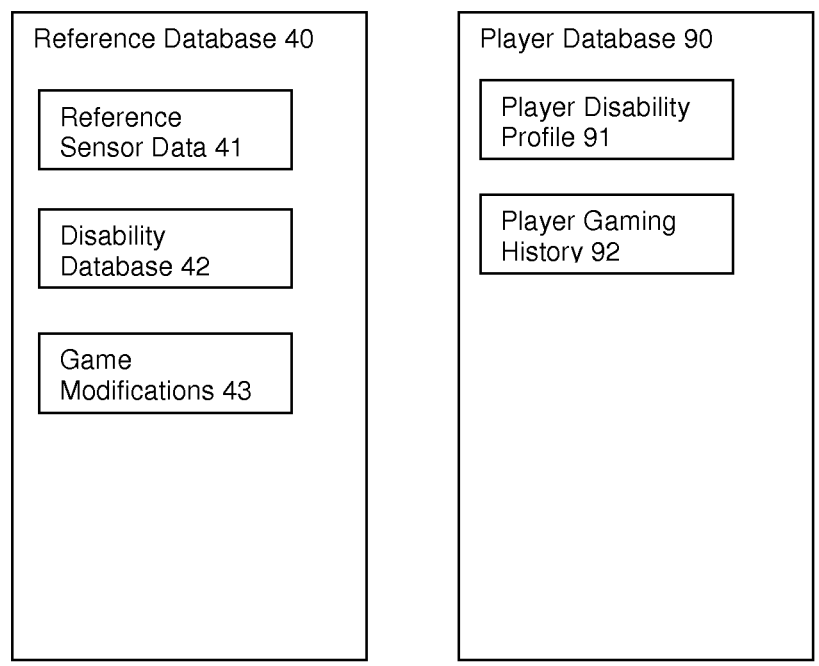
FIG. 2 shows a reference database and a player database, and the data that can be contained within each database.

The system can also include one or more of a reference database 40 and a player database 90, shown on FIG. 2.

The reference database 40 can be used to store reference data sets used in the determination of a disability status. The reference database 40 can be stored in a memory device accessible by the gaming analysis engine 80. The reference database 40 can be stored a memory contained within or external to the gaming analysis engine 80, the game system 60 or the user interface 30.

The reference database 40 can store data include one or more of reference sensor data 41, a disability database 42, and one or more game modifications 43.

The reference sensor data 41 contains reference information used in determining how the received sensor data relates to a disability. The reference sensor data 41 can contain reference sensor signature attributes. The reference sensor data 41 can be data representing baselines against which received sensor data is compared.

The disability database 42 is used to correlate received sensor data with a disability. The disability database 42 can contain data entries regarding the ascertainable disabilities (and can also include their severity levels), identified by disability indicators, and the sensor data required to determine the existence of a particular disability. The disability database 42 can also contain deviation ranges for each disability indicators, corresponding to a range of a deviation from reference sensor data corresponding to the disability indicator.

The game modifications 43 include one or more game modifications to be implemented in response to determining a disability status.

The system can include a player database 90. The player database 90 can be stored in a memory device accessible by the gaming analysis engine 80 or the game system 60. The memory device storing the player database system 90 can be a memory contained within or external to the gaming analysis engine 80, the game system 60 or the user interface 30. The player database 40 can be a player disability database and include a player disability profile.

The player database 90 can include one or more of a player disability profile 91 and player gaming history 92. The player disability profile 91 can include data regarding prior sensor measurements and prior determinations of a game player's disabilities via disability statuses and disability indicators. The player gaming history 92 can include a player's historical game playing data that is reflective of a player's experience or skill level with the gaming environment.

The reference database 40 and player database 90 can be integrated into a single database. For example, the reference database 40 can be a part of the player database 90 or vice versa.

The sensors 10 are configured to generate sensor data related to a game player's measurable parameters, characteristics and conditions during a game player's interaction with a gaming environment. The sensors 10 communicate the sensor data to the gaming analysis engine 80. Examples of sensors include accelerometers, heart rate and blood pressure sensors, respiration rate sensors, sound or light sensors, cameras, motion sensors, pressure sensors, player input sensors, galvanometers, magnetometers, piezoelectric sensors, Hall effect probes, air sensors, flow meters, chemical sensors, breathalyzers, electrocardiography sensors, spirometry sensors, sweat sensors, humidity sensors, magnetic resonance imaging sensors, blood glucose detectors, or the like.

The sensors 10 can be sensors used for a game player's interaction with the gaming environment. Examples of this type of sensor include sensors within a game controller that detect button presses from a user to cause an in-game effect. Alternatively, the sensors 10 used to gather the sensor data can be sensors completely independent of, and that have no direct interaction with, the gaming environment.

The sensors 10 can be sensors attached to the game player's body. For examples, sensors can include sensors that can be attached onto a user's body via mechanical fasteners such as clips, wrapped around a player's body parts, attached to a user's body via adhesives, and that can be swallowed or otherwise introduced into the body. The sensors 10 can be sensors attached to or embedded within the game player's clothing. For example, sensors can be located in shoes, gloves, hats, shirts, pants, jewelry, headphones and the like in order to provide sensor data about virtually any point on the user's body The sensors 10 can be sensors specifically designed to measure or detect a game player's physical, sensory, intellectual, psychological, emotional, mental, developmental, cognitive, learning, motor, social or neurological abilities, such as sensors specifically designed to be used in a hospital or medical setting. The sensor data received from these sensors can reflect a measurement of specific parameters related to the physical, sensory, intellectual, psychological, emotional, mental, learning, motor, cognitive, developmental, social or neurological conditions or abilities of the game player and the sensor data can include data, processing or formatting associated with the specialized sensor. The sensor data from this type of sensor can also include data related to one or more conclusions or decisions that the sensor can be capable of making on its own.

In addition to the measurement information representative of the sensed condition or activity itself, the sensor data can also include metadata. The metadata can include data such as a sensor identifier, a sensor type identifier, sensor configuration data, timestamp information indicating a specific time or a range of time when the sensor data was acquired, a data format identifier, encryption information, and the like.

The game system 60 can comprise a computing device configured to execute game programs, allowing the user to play video games. The user can interact with game system 60 through the user interface 30, an interface of the game system 60 itself, or another suitable interface. The game system 60 can be one or more of a gaming console, a handheld game system, a tablet, a computer, a cellular phone, a coin-operated arcade game or any other computing device configured to execute a game program.

The game system 60 can include a display monitor. The game system 60 can include audio-visual outputs that can be communicatively coupled to a display device, such as a television, allowing for the audio-visual presentation of the executed game programs.

In an embodiment, the game system 60 can be a cloud-based or online gaming service located remotely from one or more of user interface 30, gaming analysis engine 80 and sensors 10 and connected to one or more of user interface 30, gaming analysis engine 80 and sensors 10 via a long-range communication interface such as the Internet.

In an embodiment, the game system 60 can be an online gaming infrastructure. In this embodiment, users can connect to the game system 60 via user interface 30. The users can then use the game system 60 to access features such as online multiplayer gaming, game and system updates, game demos, game downloads, etc. Examples of online gaming infrastructures include Xbox LIVE, from Microsoft Corporation of Redmond, Wash.

The gaming analysis engine 80 is programmed to receive and process sensor data, and based on the received sensor data, evaluate the existence and extent of a disability in a game player or user. In response to determining the existence and extent of one or more disabilities, the gaming analysis engine 80 can cause at least one of the game system 60 and the user interface 30 to implement one or more game modifications that will modify the gaming environment, thereby making the gaming environment more accessible and enjoyable to the user having the disabilities.

The gaming analysis engine 80 can comprise a stand-alone hardware device having memory communicatively coupled to one or more processors. The memory can store computer-readable instructions that are executed by the processor(s) to carry out functions related to the inventive subject matter. The gaming analysis engine 80 can further include one or more communication interfaces that enable the gaming analysis engine 80 to exchange data with other components within the system.

The gaming analysis engine 80 can comprise a dedicated hardware processor programmed to carry out functions related to the inventive subject matter, and can be contained within the game system 60, within the user interface 30 or within another computing device communicatively coupled to the system.

The gaming analysis engine 80 can be a software module containing computer instructions that, when executed by one or more processors, cause the one or more processors to carry out functions related to the inventive subject matter. The software module can be stored in a non-transitory memory within one or more of the components within the system, or stored in memory external to the system such as in optical media (e.g., compact discs, DVDs), removable flash storage devices, external hard drives, remote servers and the like. The instructions can be carried out by one or more of the processors within one or more components of the system. For example, the gaming analysis engine 80 can be stored in the memory of the user interface 30 or the game system 60 and carried out by one or more processors within the user interface 30 or game system 60.

A user interface 30 is used by the user to interact with the game system 60, such as for the purposes of playing a game. The user interface 30 can detect user input and communicate the detected input to the game system 60 and the gaming analysis engine 80. The user interface 30 can also be used to interact with the gaming analysis engine 80. The user interface 30 can also be used to relay information between one or more sensors 10, the game system 60 and the gaming analysis engine 80. Examples of user interface 30 include one or more of a game controller, a game console, a cell phone, a handheld game device, a computer, a tablet, a keyboard, a mouse, an augmented reality interface, a virtual reality interface, a hands-free interface and a microphone.

In an embodiment, the user interface 30 can comprise one or more of the sensors 10. The user interface 30 can include the use of sensors to track the movements of a controller in 3-D space. An example of this type of interface is the interface used for the Wii game system by Nintendo. The user interface can be camera-based, where the camera can track a player's movement or can track the movement of a piece of hardware in 3-D space. Examples of this type of user interface include the Kinect interface from Microsoft or the Playstation Move interface from Sony.

The user interface 30 can include sensors 10 typically used to detect user interaction as inputs for game play, such as sensors to detect button presses and movement of digital or analog sticks. The sensors 10 can be analog or digital sensors and can include pressure sensors. Other sensors 10 within the user interface 30 can include accelerometers, touchpads, touchscreens, microphones that are typically used for game play interaction. The sensor measurements associated with user inputs related to game play can also be used by the gaming analysis engine for the methods related to the present inventive subject matter.

The user interface 30 can include one or more communication interfaces allowing for the connection of the user interface 30 with one or more sensors 10. For example, a game controller can have a connection port allowing for the connection of a microphone headset that enables a user to communicate with other players during online sessions.

The user interface 30 can include a display monitor. The user interface 30 can include audio-visual outputs that can be communicatively coupled to a display device, such as a television, allowing for the audio-visual presentation of the executed game programs.

The gaming environment can include the game system 60 and the user interface 30. The gaming environment can also include the computer game that is played via the game system 60 or user interface 30. The gaming environment can also include a display (e.g., a television, appliance display, kiosk, projection system, etc.) connected to the game system 60 or the user interface 30, used to display the visual aspects of the current game. The gaming environment can also include the environment in which the game player interacts with one or more of the game system 60, the user interface 30 and one or more sensors 10. For example, the gaming environment can include the room in which the game player plays games.

The gaming environment can further include one or more of the sensors 10 and the gaming analysis engine 80. Alternatively, the gaming environment can be independent of one or more of the sensors 10 and the gaming analysis engine 80.

A game player's disability status represents the existence and extent of a game player's disabilities such that the gaming environment can be modified in response to those disabilities. The disability status can be a listing of one or more disabilities that a game player has been determined to have based on the received sensor data. The disability status can also be data acting as an identifier or pointer to one or more modifications corresponding to particular disabilities.

The disability status can be comprised by one or more disability indicators. The disability indicators can correspond to a particular disability, and can also include a severity level of the particular disability.

The disability indicator can also be an indicator of no disability. This can be indicated by a designated disability indicator or can be indicated by a null value of a disability indicator.

The disability indicated by a disability indicator can include physical, sensory, intellectual, psychological, emotional, mental, developmental, cognitive, learning, motor, social or neurological disabilities. The disability can be a medically recognized diagnosable disability. A medically recognized diagnosable disability includes disabilities that have been officially recognized or categorized by governmental or medical authorities. For example, a particular condition as meeting a statutory or regulatory definition of "legal blindness".

The disability indicated by a disability indicator can be an indicator of a temporary disability. A temporary disability can be a disability whose effects are not permanent, where the game player makes a recovery to a prior disability status. Examples of a temporary disability include fatigue, pregnancy, the influence of drugs, alcohol or medication, temporary illness (e.g., a cold, food poisoning, lethargy, etc.), chronic illness, allergic reactions, or a temporary injury (e.g., a broken arm, muscle pulls, etc.).

In an embodiment, the disability status can be determined by mapping a sensor signature derived from the sensor data to a disability indicator that is indexed by sensor signature attributes.

In this embodiment, the sensor data can be used to derive a sensor signature. The sensor signature can comprise one or more sensor signature attributes. The sensor signature attributes can be characteristics or parameters of the sensor data. Sensor signature attributes can include image data, audio data, sensed range data, sensed measurement data, sampling duration data, sampling frequency data, and any other data related to the sensed condition or action. The sensor signature attributes can also include metadata. The metadata can include data such as timestamping data, a sensor identifier, a sensor type identifier, sensor configuration information and a data format identifier.

Figure 3:
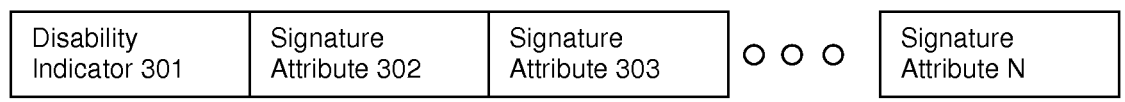
FIG. 3 shows an example entry of a disability indicator within a disability database.

FIG. 3 shows an example entry 300 within a disability database. The disability database can correspond to the disability database 42 shown in FIG. 1. As shown in FIG. 3, the entry 300 includes a disability indicator 301 and one or more sensor signature attributes 302A-302N (collectively referred to as sensor signature attributes 302). The one or more sensor signature attributes 302 are used to index the disability indicator 301 within the disability database.

Disability indicator 301 can be associated with sensor signature attributes 302 of different sensors or sensor types. For example, sensor signature attribute 302A may have been derived from sensor data received from an accelerometer and sensor attribute 302B may have been derived from sensor data received from an audio sensor.

A particular sensor signature attribute can be associated with more than one disability indicator, and thus be used to index more than one disability indicator.

After deriving the sensor signature for received sensor data, the gaming analysis engine 80 can perform a mapping of the sensor signature to a disability indicator by sensor signature attributes. The gaming analysis engine 80 can perform the mapping by matching or performing a lookup of the derived sensor signature within the sensor signature attributes. The matching or lookup function returns one or more disability indicators indexed by the sensor signature attributes.

In some cases, a disability indicator can have one or more required sensor signature attributes among all of the sensor signature attributes used to index the disability indicator. In these cases, a disability indicator will not be returned if the sensor signature from the received sensor data does not contain the required sensor signature attributes, even if all other "non-required" sensor signature attributes are present. For example, if the sensor signature attributes 302A and 302B are required sensor signature attributes for disability indicator 301, then the disability indicator 301 will not be returned if the derived signature of received sensor data does not contain both of the required sensor signature attributes 302A and 302B.

A disability indicator 301 can be representative of a particular disability. The severity of the disability can be determined by an analysis of how many of all possible sensor signature attributes 302 of a disability indicator 301 are matched by the received sensor data. If required sensor signature attributes are present, the required sensor signature attributes are used to confirm the existence of the disability and matching additional sensor signature attributes can then be indicative of an increasing severity of the disability.

A disability indicator 301 can represent both the disability and the severity. A particular disability can be represented by a plurality of disability indicators, where each individual disability indicator corresponding to a degree or stage of severity. A particular set of sensor signature attributes may be applicable to multiple levels of severity of a disability, and thus return multiple disability indicators for the same disability, but of different severity levels. The gaming analysis engine 80 can be programmed return only one of the disability indicators according to a pre-determined priority. For example, priority rules can be configured to return the disability indicator for the most severe disability level, least severe disability level, etc.

A sensor signature attribute can also be indicative of a characteristic or symptom of a disability. The gaming analysis engine 80 can determine a disability by performing a clustering analysis of the sensor signature attributes belonging to the sensor signature derived from the received sensor data. The identified clusters of sensor signature attributes correspond to disability indicators.

In an embodiment, a disability indicator can be derived from the sensor data and one or more sets of reference data from reference database 40. The reference data used in deriving a disability indicator can be a combination or collection of various available reference data sets.

The gaming analysis engine 80 can conduct a comparison of received sensor data with one or more reference data sets. The comparison of the received sensor data and the reference data results in a difference corresponding to a deviation of the received sensor data from the reference data. The deviation can be expressed as a percentage, or by values associated with the sensor data being analyzed. The gaming analysis engine 80 can then use the calculated deviation to look up the applicable disability indicator.

The reference data within the reference data sets includes data representing pre-defined or measured historical baselines of one or more data types associated with a game player's interactions with a gaming environment. A disability indicator can be indexed according to one or more deviations from the reference data sets.

Reference data can represent sensor data that corresponds to a game player that has no disabilities. This reference data can be generated based on aggregating actual sensor data gathered corresponding to one or more players known to have no disabilities. This reference data can alternatively be generated according by using information established by recognized organizations such as medical organizations, governmental organizations, professional organizations etc. For example, the reference data corresponding to a temperature sensor can be established according to what an established medical authority recognizes as the average body temperature of a healthy person having no disabilities.

Similarly, reference data can also represent sensor data corresponding to a game player having one or more known disabilities, with the reference data reflecting the limitations suffered by a game player having a particular disability. Further, the reference data can include representations of degrees or severity of a disability.

Reference data can represent sensor data corresponding to game players of various skill levels. Players of different skill levels will typically interact with and react to a gaming environment differently. For example, a novice player might become more nervous or excited while playing a game, have worse reaction times, or be more unfamiliar with a game controller than a more experienced player. The behaviors of a novice player can share similarities with the behaviors of a more experienced player having a disability. The ability to use reference data representing matching the skill level of the game player reduces the chances of a false determination of a disability.

Reference data can be historical data about the game player interacting with the gaming environment. The game player's historical data can be data stored within a player disability profile 600, described in further detail below. Using a game player's historical data as reference data sets enables a gaming analysis engine 80 to accurately track of the evolution of a game player's disability over time. The historical game player data used as reference data can be stored in reference database 40 or player database 90.

One or more reference data sets within the reference database can be used as adjustment factors for the received sensor data or other reference data sets. For example, a player's skill level or experience with a particular game can allow the player to anticipate situations in the game. A game player anticipating a game situation enables the player to react to the game situation faster than if the player were to be surprised by the situation. If sensor data is being gathered related to a game player's reaction time, the player's ability eliminate the surprise element will result in sensor data that does not represent an accurate measurement of the player's true ability to react. To adjust for this, reference data from a player's profile that reflects the player's experience or skill with the game can be used to adjust the sensor data prior to the comparison with the sensor reference data sets, to "correct" for the player's ability to avoid the in-game surprise. For example, the adjustment factor can be a scaling factor in a function using at least a portion of the sensor data as input, where the output is adjusted sensor data.

In an embodiment, the sensor data can be used to derive a sensor signature having sensor signature attributes as discussed above. In this embodiment, the reference data contains reference sensor signature attributes. The disability indicators are indexed according to differences corresponding to deviations from the reference sensor signature attributes. The sensor signature attributes from the derived sensor signature are compared to the reference signature attributes to determine a deviation, which is then used to retrieve the corresponding disability indicator via a lookup function.

In an embodiment, the reference database 40 can contain the entries for one or more sensors 10 that are determined to be connected and operational by the gaming analysis engine 80 via the execution of a diagnostics process, and also contains the disability indicators that can be indexed from these sensors 10. The reference database 40 can also include entries for one or more sensors 10 that are applicable to the particular gaming environment but that are not active or currently connected. The reference data included in the reference database 40 for a particular system can be retrieved from a master reference database containing all the possible sensors usable in all gaming environments and all the possible disabilities and their severity levels that can be determined from all of the possible sensor and sensor combinations.

The reference data sets contained in reference database 40 can be further distilled into database views centered on a particular sensor or a particular disability.

The disability database 42 within the reference database 40 can include data sets containing entries correlating disabilities with the sensor data necessary to determine their existence. The data sets can include deviation data used to identify a disability indicator corresponding to deviations between received sensor data and reference data.

FIG. 4 provides an example of a deviation data set in the form of a sensor deviation data set 400 that can be used in the determination of one or more disability indicators 401*a*-*d*, 402*a*-*c* and 403*a*-*c*. The deviation data of the deviation data set can be populated with data stored in the disability database 42 shown in FIG. 2.

The sensor deviation data set 400 can correspond to sensor data from a specific sensor (i.e., a specific sensor unit of a specific make or model) or sensor data associated with a sensor type or sensor data type (e.g., sensors used for a specific type of measurement, such as thermometers, sensors whose data readings and output are standardized as part of a widely used protocol, or sensors whose data readings and output are provided in a standardized unit of measurement).

The sensor deviation data set 400 can represent sensor data attributes. As described above, the sensor data attributes can represent common characteristics of sensor data from sensors of different types.

The sensor deviation data set 400 can include entries for deviation ranges in the column labeled "Deviation Range". In FIG. 4, an illustrative example of ranges is provided in the form of percentage ranges. However, the ranges can alternatively be ranges of values quantifying the deviation. The columns 401, 402 and 403 can represent disabilities, with the individual entries of the columns containing a disability indicator corresponding to a disability and severity. The disability indicators of columns 401, 402 and 403 are indexed according to deviation ranges. After determining a deviation of the received sensor data from the reference data, the gaming analysis engine 80 can identify a disability indicator corresponding to the deviation by mapping the deviation to the deviation range that includes the deviation.

The deviation ranges can be in positive or negative values. A negative percentage deviation can be indicative of an improvement in a game player's condition, reflecting a game player overcoming a disability via treatment or rehabilitation Likewise, a negative deviation can be indicative of a game player overcoming a temporary disability, and returning to a prior status of health.

The first row shown in FIG. 4 includes a range of 0%-10%. This first row can be a range representing a deviation returning no disability. This can be represented in the form of a disability indicator such as 401*a* or 403*a*. Alternatively, the return of no disability can be in the form of a null value, illustrated in first row entry of column 402. The disability indicator 401*a* can alternatively be a historical or past disability indicator determined previously. In this case, the deviation range of 0%-10% returns a disability indicator 401*a* that indicates there is no change in that aspect of the disability status from the last time the determination was performed.

FIG. 4 also shows a row that represents a maximum deviation (here, "Over 100%"). Deviations beyond this maximum do not affect the determination of a disability. This maximum deviation can represent a "worst case" or "absolute case", where the disability is at its most severe stage.

In some cases, the deviation required to establish the maximum level of severity can be different from one disability to another. As shown in FIG. 4, disability indicator 403*c* is repeated because a deviation of more than 20% from the reference data is indicative of the maximum severity for the disability of column 403. Therefore, any deviation of more than 20% will return the maximum severity indicator 403*c*.

FIG. 5 provides an example of a reference data set representing a disability 501. The data set 501 can include entries for disability indicators 501*a*-501*n* representing the severity of the disability. The columns 502-504 represent the reference sensor data required to determine the different severity levels of the disability 501.

The gaming analysis engine 80 calculates deviations based on received sensor data and reference sensor data 502, 503 and 504. The calculated deviations can be mapped to the deviation ranges 502*a-n*, 503*a-n* and 504*a-n*, respectively, to determine the corresponding disability indicator 501*a*-501*n*.

The determination of the existence and severity of a disability may not require all of the sensor data 502-504 listed in a particular reference data set. In these cases, the sensor data types required to ascertain a disability can be prioritized according to importance. The sensor data 502-504 can be assigned weights according to the importance of the sensor type in the determination of the disability. Likewise, the determination of a particular disability can require sensor data from one or more data types, without which the determination is not possible. If sensor data from one of these data types is missing or unavailable (e.g., if the sensor is non-functional), the disability indicator for that disability will not be returned.

In some cases, a lack of sensor readings or sensor data from a functional sensor of a required sensor type can be indicative of an extreme severity of a particular disability (i.e., a sensor registered no readings because the game player lacks the body part to perform an action detectable by the sensor). In these cases, a determination of the existence of the disability (i.e., 100% disability of a particular body part or body function) can be made regardless of any other available sensor data, and the disability indicator indicating the maximum severity of the disability will be returned.

Figure 6:
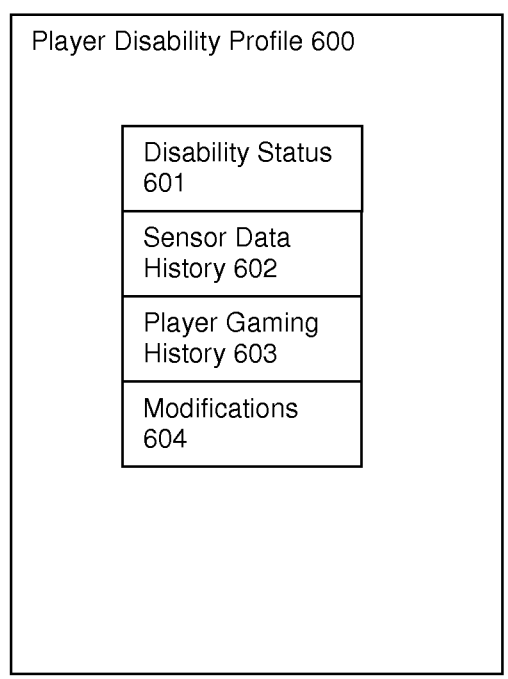
FIG. 6 is an example of a player disability profile.

FIG. 6 provides an example of a player disability profile 600. The player disability profile 600 corresponds to the player disability profile 91 shown on FIG. 2.

The player disability profile 600 can include one or more sets of player-specific historical data regarding a player's potential disability. The player disability profile 600 can include a disability status 601, sensor data history 602, player gaming history 603 and player-specific modifications 604.

The disability status 601 can represent a "current" disability status and be updated to reflect the most recently received sensor data. The disability status 601 can also have historical data indicating a game player's past disability statuses. The disability status 601 can also include current and past disability indicators that comprise current and past disability statuses 601, respectively.

The player gaming history 603 can include information reflective of the game player's skill and experience with the gaming environment such as time logged with the gaming environment, time logged with individual games, completion indicators related to individual games, unlocked awards, win-loss records, and a score or other indicator of a game player's experience or skill. Other data reflective of a user's past behaviors can also be included in a game player's disability status, such as indicators of favorite games or genres, purchase or download history, list of friends or organizations within the gaming environment that the user frequents or interacts with, etc.

The information within the player's disability profile can be used in a variety of ways. As described above, the information within the player's disability profile can be used as reference data. The disability status 601 or the past sensor readings 602 can be used as reference data sets for comparison with a newly-collected set of sensor data. Comparing newly-acquired sensor data to that game player's historical data allows for accurate determinations of the game player's evolving disability status.

For a game player whose past sensor readings 602 consistently result in a determination of "no disability", but whose sensor readings 602 consistently deviate from the center or mean of the reference data, the past sensor readings 602 can provide an adjusted baseline that correspond to "normal" readings for that specific player. This can allow for the adjustment of the ranges that would result in the determination of a disability for that specific player. This can also assist in error detection by preventing modifications to the gaming environments due to false positives.

The use of data from a player disability profile 600 can also assist in the determination of a temporary disability. For example, a game player having an established disability status 601 interacts with a gaming environment. During this interaction, sensor data is received and from the data, a new disability status is determined. This sensor data is then added to the historical sensor data 603 of a game player's disability profile. In future interactions with the gaming environment, sensor data will be received and analyzed accordingly. If the analysis of the future sensor data results in the disability status returning to the previously established status 601 (i.e. the sensor data resulting in the new disability status is a statistical outlier given the prior and subsequent sets of received sensor data), it can be an indication that the new disability status was a temporary disability status. Because the sensor data and analysis thereof can be performed as often as desired or necessary, the existence of extremely short temporary disabilities and recovery therefrom can be ascertained (such as drowsiness/fatigue). Additionally, the existence of statistically outlying sensor data occurring periodically at regular intervals can assist in determining a particular type of temporary disability. For example, if sensor data indicating the same new disability occurs after 1:00 AM every night or occurs every Friday evening, the disability can be determined to be the temporary disability of fatigue due to being up too late at night or resulting from the end of a work week.

For a game player having a previously determined disability indicated by disability status 601, the use of historical sensor readings 603 or disability status 601 can assist in tracking the evolution of the player's disability, including changes in severity of a disability or the emergence of related disabilities. This can assist the treatment of the player's condition by providing measured data reflecting the changes in a game player over time.

The player disability profile can be included into traditional game player profiles (such as those provided by the Xbox LIVE service). Alternatively, the player disability profile can be separate from the traditional gamer profile and configured to draw data from the traditional gamer profile. As another alternative, the player disability profile can include the traditional gamer profile.

Upon the determination of a disability status, the gaming analysis engine 80 can cause a modification or change of the gaming environment. The modification can be implemented in the form of a game modification 43.

A game modification 43 can be a change to one or more aspects of the gaming environment. The game modification 43 can comprise an instruction or command set sent by the gaming analysis engine 80 to at least one of the user interface 30 and game system 60, and executed by at least one of the user interface 30 and the game system 60. The execution of the game modification causes at least one of the user interface 30 and the game system 60 to implement changes to their functions, thus modifying the gaming environment. The game modification 43 can also include instructions to retrieve additional content that is implemented as part of the modification. Alternatively, the game modification 43 can include the additional content to be implemented along with the instruction set.

A game modification 43 can be indexed by or otherwise associated with one or more disability statuses or one or more disability indicators.

The game modification 43 can include one or more of a change to the current game being played, a change to the configuration of the user interface 30 or a change to the configuration of the game system 60. These changes can improve the game-playing experience of the user having the disability by reducing the effect that the game player's disability has on the interaction with the gaming environment.

The modification 43 can be an instruction to create, destroy, activate, deactivate, update, increase, reduce, adjust, change over time, change according to trends, convert, transform, delete, insert, overlay, write, or overwrite.

Changes to the current game being played can include adjusting game play factors such as the game's difficulty (in one or more of single-player and multi-player games), the game play speed, the game's appearance (e.g., adding or enlarging text or other graphics, changing the colors to account for color-blindness, providing visual cues to match audio, etc.), the game's audio (e.g., prioritizing the output of certain audio over others by volume or by removing lower-priority audio, etc.), the mapping of inputs to game play functions (e.g., changing the mapping of game play functions to the button layout of the controller to change the function of the buttons, allowing a player to hold down a particular button instead of pressing it repeatedly, etc.), providing A.I. assistance for certain game play functions or in certain game situations, providing in-game advantages, an output modality conversion (e.g., converting audio output into visual output, converting visual output into audio output, etc.) and the like.

The game modification 43 as applied to the current game can be in the form of content within the game program adapted for use by a game player depending on the existence and extent of one or more disabilities. The content can be included with the game program or added to the game program via patches or updates. The content can include sets of pre-defined changes, such as pre-defined configurations or profiles that correspond to particular disabilities.

Changes to the configuration of the game system 60 can include changes such as those described above for a current game, applied to the aspects of the game system 60 outside of the current game. For example, changes implemented to the current game can also be applied to navigating system menus outside of games and for performing non-game tasks. In addition, the use of system-wide adaptations allow for the application of the changes to multiple games without requiring the disability determination process to be carried out from scratch for each game played.

Changes to the configuration of the game system 60 can include adjusting access permissions for features of the game system. Examples include adjusting access permissions for features such as online play (e.g., whether the game player can access an online gaming environment at all, which games or genres of games the player may play online, the level of privacy or visibility to other players within the online environment, limitations on who the player may interact with, etc.), content that can be accessed by the player using game system 60 (e.g., genres of content, types of contents such as games, music, videos, etc., specific games, age-specific categories of content, etc.) and time duration of gaming sessions.

Changes to the configuration of the user interface 30 can include automatically adjusting the sensitivity of the user interface's inputs (analog and digital buttons and joysticks, accelerometers, motion detection, etc.), changing the intensity of or disabling vibration functions, and adjusting or disabling sensory feedback functions (e.g., speakers, display screens, etc.), or otherwise change how the game player interacts with the user interface 30 or how the user interface 30 interacts with game system 60.

Changes to the gaming environment can include the disabling or powering down one or more aspects of the gaming environment. For example, if it is determined that a game player suffers from a disability whose effects or symptoms can be triggered or aggravated by the game player's interactions with the gaming environment (e.g, epilepsy, anxiety disorders, etc.), the game modification can cause one or more of the termination of the current game, the disabling or powering off of the user interface 30 and the disabling or powering off of the game system 60.

Changes to the gaming environment can also include an adjustment of the display device (such as the television) used for the visual and audio output of a game. The changes to the display device can include changing functions or settings related to audio functions (e.g., volume, mute, output channels, surround sound settings, stereo settings, equalizer settings, secondary audio channels, etc.) and video functions (e.g., colors, contrast, resolution, aspect ratio, refresh rate, brightness, source selection, picture-in-picture, closed captioning, etc.).

In addition to improving the gaming experience for a person having a disability, the game modification 43 can also change the gaming environment to account for a game player's disabilities for other purposes, such as power conservation or processing and networking efficiency. For example, if a game player is deaf, the modification may disable the audio output functions of the game system 60 or the user interface 30. This can conserve battery life for a battery-operated user interface 30 by eliminating the need to activate a speaker function of user interface 30. Likewise, the processing bandwidth typically allocated to processing audio functions can be allocated to other functions and, in a networked environment, the network bandwidth required by the gaming environment is reduced by eliminating the transmission of data associated with audio functions.

The game modification 43 can include contacting health or emergency personnel based on the determined disability. Emergency personnel can be contacted via communication interfaces of at least one of the gaming analysis engine 80, the game system 60 or user interface 30.

As described above, the disability status of a game player can indicate a temporary disability. In the case of a temporary disability, the game environment may be adjusted differently from a permanent disability, or not be adjusted at all. For example, modifying a game because a game player is tired or intoxicated may be considered unfair to other players of the game, and thus the gaming analysis engine does not implement a modification for this type of disability.

The game modification 43 can include a modification of the gaming environment to implement changes related to therapeutic or rehabilitation activity. For example, if a game requires a user to generate certain motions using a user interface 30 having motion detection as an input for interaction with the game, the game modification can modify one or more of the motions required by the game to a motion that is performed as part of a therapy or rehabilitation program by a patient recovering from an injury or other type of disability.

A game modification 43 can comprise accessing a recommendation engine configured to recommend a particular game based on the existence and extent of a disability. The particular game can be a game that is similar to the current game, but that requires a lesser modification. The particular game can also be a game having features specifically designed for game players having the disability.

Figure 7:
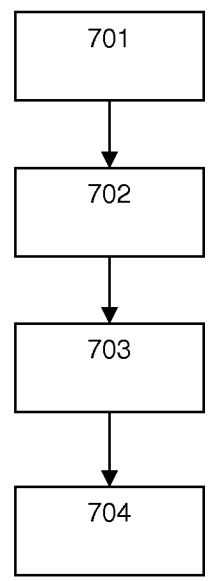
FIG. 7 is a flow chart illustrating a method of modifying a game based on a detected disability status.

FIG. 7 is a flow chart depicting an exemplary execution of method of modifying a game based on a detected disability status.

In step 701, the gaming analysis engine 80 receives sensor data captured by one or more of sensor(s) 10.

In step 702, the gaming analysis engine 80 can determine if one or more possible disabilities exist, and if so, the extent of the possible disabilities by determining a disability status. The determination of the disability status can be performed according to one of the methods described above. In this example, the disability status is performed by a comparison of the received sensor data to reference sensor data retrieved from reference sensor database 41. The comparison results in deviation values for each of the sets of sensor data received. the gaming analysis engine 80 maps each the calculated deviation values to the corresponding deviation value range in which each of the values falls. This mapping returns a set of disability indicators, which are grouped together to return a disability status.

In step 703, the gaming analysis engine 80, at least partially in response to or as a function of the determined disability status, causes the implementation of a game modification. The game modification to be implemented can be retrieved by identifiers of the disability status.

At step 704, the game modification is implemented by one or more of the game system 60 and the user interface 30 and the gaming environment is adjusted accordingly. Either prior to or after the implementation of the game modification, the newly-determined disability status, as well as the disability indicators and received sensor data can be saved to the reference database 40 and player database 90 as appropriate to properly update the stored data.

The method can be conducted as often as necessary to properly determine the existence and severity of one or more disabilities and to be able to track the evolution of the disability over time. For example, the process can be carried out upon a player's initiating an interaction with the gaming environment. The process can then be carried out periodically after that or upon certain triggering conditions occurring (e.g., the game player starting to play a new game). In another example, the process can be carried out as a calibration step related to the gaming environment. Alternatively, the process can be initially carried out as a series of instructions to specifically determine an initial disability status. After the initial determination, the process can be repeated during the game player's interactions with the gaming environment.

A frequent repetition of the method can also be used to determine the existence of a temporary disability. A sizeable change in the disability status of a game player during the same gaming session can be indicative of a temporary disability, such as the game player becoming fatigued over time.

The gaming analysis engine 80 can also include verification and validation functions, to ensure accuracy of the determination of a disability and of the subsequent implementation of the appropriate modification in response to the disability. The verification and validation functions can include comparing the determined disability with a game player's medical history to ensure that the disability determination is reasonable given the game player's medical history. The verification can be performed by the gaming analysis engine 80, by requesting and receiving a game player's medical history information from a provider. Alternatively, the verification can be performed by a separate processing system (such as one belonging to a medical provider), with confirmation sent to the gaming analysis engine 80 after the determination.

The following are examples of uses of the systems and methods of the present inventive subject matter. The examples are illustrative, and are not intended to limit the scope of the inventive subject matter, or to be interpreted as limiting the inventive subject matter to only these uses. Likewise, and unless otherwise expressly indicated, the language used in the examples is to assist in the understanding of the examples and is not to be interpreted as providing definitions or lexicography.

In an example, a game player begins to play a game on a gaming console using the game controller supplied with the game console. For regular gameplay, the game requires a player to interact with the game controller's buttons and control sticks. As the game player is playing the game, the gaming analysis engine collects data from the controller's sensors associated with the buttons and control sticks. The collected data reveals that that the sensors associated with buttons and control stick on a particular side of the game controller are very rarely activated when they should be activated during the playing of the particular game (or not activated at all), whereas buttons and control stick on the other side of the game controller are activated within an acceptable range for regular gameplay. Based on this data, the gaming analysis engine determines that the game player has a disability associated with one hand that prevents the player to interact with the particular side of the controller. In order to allow the game player to be able to better interact with the game, the gaming analysis engine can respond by interacting with the game system to change the controller configuration used in interacting with the game system or the game. The change of the controller configuration can be a mapping of the inputs associated with the unusable buttons and control stick to the buttons and control stick the user can access with their abled hand. This allows the game player to be able to control the game entirely with one hand. Additionally, the gaming analysis engine can reduce the amount of vibration feedback provided by the controller (or disable the vibration feedback altogether), to reduce the risk that a user with only one abled hand will lose their grip on the controller and drop it.

In an example, the system is used to track a user's disability over time. A game player first interacts with the system, which determines that the game player has a disability of a relatively low severity level. Over time, the game player accesses the gaming environment to play games and the gaming analysis engine uses data gathered from sensors during each gaming session to conduct new determinations of a disability, in part by comparing the new data with the data of previous gaming sessions. As the game player's disability gets more severe, the gaming analysis engine can adjust the modifications required to allow the user to interact with the gaming environment and a similar level. The newly determined status is saved into the player's historical records, and can be provided to health care providers responsible for helping the game player with the treatments of the disability. Having an accumulated user history available to a health care provider allows for the gathering of data without requiring the game player to report to a medical facility as frequently for tests. Also, the game player's treatment is optimized because the game player is providing measurement data in a way that is transparent to the game player, by engaging in an activity that the game player would otherwise engage in for recreation.

In an example, a game player is playing a game. Over time, the system recognizes that the game player's in-game performance is decreasing, and the sensor data indicates that the game player is showing delayed reaction times to in-game situations. The system realizes that the game player has been playing for several hours, and that the current time is about 2:00 AM. The system retrieves the player's disability profile and notices that the game player does not have a recognized disability. The determination is made that the game player is tired, and because the disability is merely exhaustion and that it is temporary, the system does not implement any modification to any aspect of the gaming environment. Alternatively, in view that the player is experiencing some difficultly, the system can modify the game to store or save the game state more frequently. The advantage of such an approach allows the player to access a more recent restore point without the frustration of possibly repeated losses.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An interactive system for optimizing a gaming experience, the system comprising:
   a gaming analysis engine programmed to:
      receive sensor data from at least one sensor, wherein the sensor data comprises data captured by the at least one sensor and associated with a game player's interactions with a gaming environment while playing a computer game within the gaming environment;
      determine at least one disability status of the game player as a function of the sensor data, each of the at least one disability status being indicative of a respective disability; and
      cause a modification of the gaming environment as a function of the disability status, the modification implemented while the player is playing the computer game to improve the game player's experience by reducing the effect of the disability on the game player's interactions with the gaming environment, the modification comprising at least one of:
         an adjustment to an input detection sensitivity of a user interface; and
         a deactivation of at least one input of the user interface.

2. The system of claim 1, wherein the gaming analysis engine is further programmed to determine the at least one disability status by mapping at least one sensor signature derived from the sensor data to at least one disability indicator indexed by sensor signature attributes.

3. The system of claim 1, wherein the at least one disability status comprises at least one disability indicator derived from the sensor data and from at least one reference data set.

4. The system of claim 3, wherein the gaming analysis engine is further programmed to determine the at least one disability status by generating at least one disability indicator as a function of a difference between the sensor data and the at least one reference data set associated with the at least one disability indicator.

5. The system of claim 3, wherein the at least one disability indicator comprises an indicator of no disability.

6. The system of claim 3, wherein the at least one disability indicator comprises at least one indicator of at least one disability.

7. The system of claim 6, wherein the at least one disability comprises at least one of a physical disability, a sensory disability, a motor disability, a cognitive disability, a developmental disability, a social disorder, an intellectual disability, an emotional disability, a learning disability, a mental disability, and a psychological disability.

8. The system of claim 6, wherein the at least one disability comprises at least one temporary disability.

9. The system of claim 6, wherein the at least one disability comprises at least one recognized diagnosable disability.

10. The system of claim 3, wherein the at least one disability indicator comprises at least one indicator of at least one disability and of a severity level of the at least one disability.

11. The system of claim 3, wherein the at least one reference data set is based on at least one of:
   sensor data corresponding to a reference game player having no disabilities;
   sensor data corresponding to a reference game player having at least one disability;
   sensor data corresponding to a reference game player having at least one disability of at least one severity level;
   sensor data representative of a plurality of reference game player skill levels;
   historical game player data representative of the game player's skill level; and
   previously captured sensor data associated with the game player.

12. The system of claim 1, wherein the sensor data comprises game interface input data.

13. The system of claim 1, wherein the modification of the gaming environment comprises a modification to a game system executing the computer game.

14. The system of claim 13, wherein the modification of the game system comprises at least one of:
   an adjustment to at least one aspect of the visual output of the game system;
   an adjustment to at least one aspect of the audio output of the game system;
   a modification to at least one recognized command associated with at least one user input; and
   an output modality conversion.

15. The system of claim 1, wherein the modification of the gaming environment comprises a modification of the computer game.

16. The system of claim 15, wherein the modification of the computer game comprises at least one of:
   an adjustment to the difficulty of the computer game;
   a change to the visual appearance of at least one aspect of the computer game;
   a change to the audio of at least one aspect of the computer game;
   a modification to an interpretation of player inputs by the computer game; and
   an activation of an assistance feature of the computer game;
   an addition or subtraction of a game feature to the computer game;
   an adjustment to the game speed of the computer game; and
   an output modality conversion.

17. The system of 1, wherein the modification comprises a therapeutic modification corresponding to the disability status.

18. The system of claim 1, wherein the modification of the user interface further comprises:

an adjustment to a feedback feature of the user interface.

19. The system of claim 1, wherein the sensor data comprises data from at least one of: an image sensor, a video sensor, an audio sensor, a motion sensor, a temperature sensor, an input detection sensor, a reaction sensor, an accelerometer, a pressure sensor, a light sensor, a sound sensor, a biometric sensor, a galvanometer, a magnetometer, a piezoelectric sensor, a Hall effect probe, an air sensor, a flow meter, a chemical sensor, a breathalyzer, an electrocardiography sensor, a spirometry sensor, a sweat sensor, a humidity sensor, a magnetic resonance imaging sensor, a blood pressure sensor, a heart rate sensor, a respiration rate sensor, and a blood glucose sensor.

\* \* \* \* \*